(12) United States Patent
Caterer (10) Patent No.: US 8,507,295 B2
(45) Date of Patent: Aug. 13, 2013

(54) METHODS OF QUANTIFICATION FOR LATERAL FLOW DEVICES

(76) Inventor: Nigel Robert Caterer, Copenhagen (DK)

( * ) Notice: Subject to any disclaimer, the term of this patent is extended or adjusted under 35 U.S.C. 154(b) by 0 days.

(21) Appl. No.: 12/743,166

(22) PCT Filed: Nov. 10, 2008

(86) PCT No.: PCT/DK2008/000396
§ 371 (c)(1),
(2), (4) Date: May 14, 2010

(87) PCT Pub. No.: WO2009/062506
PCT Pub. Date: May 22, 2009

(65) Prior Publication Data
US 2011/0124127 A1    May 26, 2011

(30) Foreign Application Priority Data
Nov. 14, 2007 (DK) ................................. 2007 01608

(51) Int. Cl.
*G01N 33/543* (2006.01)
*G01N 33/558* (2006.01)

(52) U.S. Cl.
USPC ...... 436/518; 435/7.1; 435/287.1; 435/287.2; 435/287.7

(58) Field of Classification Search
None
See application file for complete search history.

(56) References Cited

U.S. PATENT DOCUMENTS

| | | | | |
|---|---|---|---|---|
| 5,567,591 | A | * | 10/1996 | Lovell et al. .................. 435/7.5 |
| 6,485,982 | B1 | * | 11/2002 | Charlton ........................ 436/514 |
| 7,659,086 | B2 | | 2/2010 | Harris et al. |
| 2002/0146844 | A1 | | 10/2002 | Pronovost et al. |
| 2003/0199004 | A1 | | 10/2003 | Fong |
| 2006/0246601 | A1 | | 11/2006 | Song et al. |

FOREIGN PATENT DOCUMENTS

| | | |
|---|---|---|
| EP | 585912 A1 | 3/1994 |
| WO | 9706439 | 2/1997 |
| WO | 0157522 | 8/2001 |
| WO | 02083894 | 10/2002 |
| WO | 2005078446 | 8/2005 |
| WO | 2006083367 | 8/2006 |
| WO | 2007011936 | 1/2007 |
| WO | 2007098184 | 8/2007 |
| WO | 2009014787 | 1/2009 |

OTHER PUBLICATIONS

Schulte "Advanced Receptor Pharmacology," citing "Pharmacology Primer" dated 2006; retrieved from http://ki.se/content/1/c6/04/97/40/Advanced%20quantitative%20receptorpharmacology.pdf on Aug. 10, 2012.*
Supplemental Search Report dated Nov. 18, 2010 in corresponding European Patent Application No. 08849860.5.
Millipore Rapid Lateral Flow Test Strips; Considerations for Product Development brochure, Millipore Corporation, Billerica, MA, 42 pages, 2008.

* cited by examiner

*Primary Examiner* — Shafiqul Haq
*Assistant Examiner* — Galina Yakovleva
(74) *Attorney, Agent, or Firm* — Fish & Richardson P.C.

(57) ABSTRACT

The invention concerns methods of quantification of an analyte, A, in a test sample by means of a single immunochromatographic device, such as a lateral flow device (LFD). One method comprises the steps of: a) mixing a determined amount of said test sample with a determined amount of a quantification agent, QA1, said QA1 being capable of binding specifically and simultaneously both to an immobilized binding partner and to A, thus obtaining a mixture wherein the amount of A in said test sample is reflected by the ratio of the concentration of A-QA1 complex formed to the concentration of free QA1 in said mixture; b) applying a determined volume of said mixture to said test device equipped with a test band in which said binding partner of the QA1 is immobilized, so that A-QA1 complex and free QA1 are immobilized at said test band in a ratio that relates to their concentration ratio in the mixture applied, said volume of mixture being determined to provide a total amount of A-QA1 complex and free QA1 capable of sufficiently saturating the immobilized binding partner in said test band; c) measuring the amount of either said A-QA1 complex or said free QA1 immobilized at the test band by means of an appropriately chosen detection procedure; d) comparing the result obtained from the test sample with the results obtained from calibration samples containing known or allocated amounts of A and thus determining the amount of A in said test sample. By including the two procedural stages a) and b) this greatly diminish or eliminate the sources of run-to-run variation.

11 Claims, 6 Drawing Sheets

|  | Response Mean | Response Standard Deviation | Number of Tests | Response change due to addition of glycerol | Student's t test (P) |
|---|---|---|---|---|---|
| Saturated control | 318 | 10 | 4 | | |
| Saturated 10% glycerol | 316 | 6.5 | 4 | 0.7% | 0.72 |
| Non-saturated control | 334 | 8.8 | 4 | | |
| Non-saturated 10% glycerol | 236 | 12.1 | 4 | 29% | <0.0001 |

Figure 3

| | Response Mean | Response Standard Deviation | Number of tests | Response change from 22°C | Student's t test (P) |
|---|---|---|---|---|---|
| Saturated 12°C | 284 | 13.2 | 3 | -7.2 % | 0.13 |
| Saturated 22°C | 306 | 15.3 | 3 | | |
| Saturated 37°C | 309 | 11.4 | 3 | 1.2 % | 0.76 |
| Non-Saturated 12°C | 229 | 18.1 | 3 | -32 % | 0.0013 |
| Non-Saturated 22°C | 336 | 14.4 | 3 | | |
| Non-Saturated 37°C | 410 | 21.9 | 3 | 22 % | 0.008 |

Figure 4

| Concentration ng/ml | Response (Ref.-test) | | | | | | Calculated Concentration ng/ml | | | |
|---|---|---|---|---|---|---|---|---|---|---|
| | T | R | R-T | mean | SD | %CV | | mean | SD | %CV |
| 1000 | 335 | 627 | 292 | 294 | 4.36 | 1.48 | 958 | 1023 | 130 | 12.7 |
| | 312 | 603 | 291 | | | | 938 | | | |
| | 326 | 625 | 299 | | | | 1173 | | | |
| 500 | 385 | 620 | 235 | 243 | 7.55 | 3.11 | 457 | 498 | 38.5 | 7.74 |
| | 367 | 611 | 244 | | | | 501 | | | |
| | 358 | 608 | 250 | | | | 534 | | | |
| 250 | 464 | 641 | 177 | 172 | 7.81 | 4.54 | 265 | 254 | 17.9 | 7.07 |
| | 430 | 606 | 176 | | | | 263 | | | |
| | 406 | 569 | 163 | | | | 233 | | | |
| 125 | 515 | 611 | 96 | 100 | 6.66 | 6.64 | 118 | 124 | 9.5 | 7.67 |
| | 489 | 586 | 97 | | | | 119 | | | |
| | 497 | 605 | 108 | | | | 135 | | | |
| 62.5 | 519 | 565 | 46 | 49.7 | 3.21 | 6.47 | 57.8 | 61.7 | 3.41 | 5.53 |
| | 526 | 577 | 51 | | | | 63.1 | | | |
| | 524 | 576 | 52 | | | | 64.2 | | | |
| 31.3 | 559 | 578 | 19 | 19.7 | 2.08 | 10.6 | 31.3 | 32 | 1.92 | 6.01 |
| | 560 | 582 | 22 | | | | 34.1 | | | |
| | 575 | 593 | 18 | | | | 30.4 | | | |

Figure 5

| Concentration µg/ml | Response (Ref.-test) | | | | | | Calculated Concentration µg/ml | | | |
|---|---|---|---|---|---|---|---|---|---|---|
| | T | R | R-T | mean | SD | %CV | | mean | SD | %CV |
| 5.50 | 121 | 658 | 537 | 547 | 14.6 | 2.66 | 5.09 | 5.45 | 0.52 | 9.52 |
| | 114 | 678 | 564 | | | | 6.05 | | | |
| | 117 | 658 | 541 | | | | 5.23 | | | |
| 2.75 | 162 | 626 | 464 | 457 | 5.77 | 1.26 | 3.01 | 2.86 | 0.13 | 4.47 |
| | 133 | 587 | 454 | | | | 2.78 | | | |
| | 159 | 613 | 454 | | | | 2.78 | | | |
| 1.38 | 226 | 594 | 368 | 361 | 13.6 | 3.76 | 1.44 | 1.37 | 0.14 | 9.92 |
| | 221 | 566 | 345 | | | | 1.21 | | | |
| | 232 | 601 | 369 | | | | 1.45 | | | |
| 0.69 | 284 | 543 | 259 | 261 | 2 | 0.766 | 0.63 | 0.64 | 0.01 | 1.53 |
| | 308 | 569 | 261 | | | | 0.64 | | | |
| | 311 | 574 | 263 | | | | 0.65 | | | |
| 0.34 | 416 | 607 | 191 | 189 | 5.29 | 2.80 | 0.36 | 0.36 | 0.02 | 4.65 |
| | 406 | 599 | 193 | | | | 0.37 | | | |
| | 380 | 563 | 183 | | | | 0.34 | | | |
| 0.17 | 445 | 579 | 134 | 129 | 5.51 | 4.28 | 0.21 | 0.19 | 0.01 | 6.50 |
| | 472 | 601 | 129 | | | | 0.20 | | | |
| | 421 | 544 | 123 | | | | 0.18 | | | |
| 0.09 | 471 | 536 | 65 | 67 | 2.65 | 3.95 | 0.07 | 0.072 | 0.005 | 6.41 |
| | 474 | 544 | 70 | | | | 0.08 | | | |
| | 472 | 538 | 66 | | | | 0.07 | | | |

Figure 6

METHODS OF QUANTIFICATION FOR LATERAL FLOW DEVICES

CROSS REFERENCE TO PRIOR APPLICATIONS

This is a U.S. National Phase application under 35 U.S.C. §371 of International Patent Application No. PCT/DK2008/000396, filed Nov. 10, 2008, and claims the priority of Danish Patent Application No. PA200701608, filed Nov. 14, 2007 both of which are incorporated herein by reference. The International Application published in English on May 22, 2009 as WO 2009/062506 under PCT Article 21(2).

FIELD OF THE INVENTION

The field of the invention is analytical biochemistry, especially the detection and quantification of specific macromolecules.

BACKGROUND OF THE INVENTION

Immunochromatographic or lateral flow assays (LFA) have existed for over twenty years and have proved to be simple and easy to use. This assay technology is characterized by exploiting the migration of a liquid sample by capillary forces through a porous or channeled solid phase so that the analyte enters into successive contact with binding molecules of which at least one is bound to the solid phase. In LFA, unlike non-automated immunoassay systems such as conventional enzyme-linked immunosorbent assay (ELISA), the process of contacting the sample with the individual test components that for example bind the analyte occurs as the fluid phase travels through the solid phase by capillary forces once the sample has been loaded, and is not carried out by the operator.

One of the most common LFA formats involves a sandwich-type assays in which the analyte is bound in between two analyte specific binding partners, Such a so called lateral flow device (LFD) consists of four serial zones of permeable material in fluid communication, illustrated in FIG. 1A. Fluid applied to the sample pad via the application well (a1) flows from the sample pad through a conjugate release pad to a test membrane and to finally an absorbance pad. Positions located closer to the outer end of the sample pad are referred to as being upstream and positions closer to absorbance pad are referred to as being downstream. However, there are a number of different LFA and LFD formats known to prior art that vary in the control of different assay-specific analytical parameters. These include non-linear, multiple path and reverse flow LFDs.

In the most common LFD, the first zone is the sample application zone and comprises a single sample pad (SP; b in FIG. 1A), to which the sample as well as other relevant aqueous solutions are applied via an application well, but there may also be more than one application well over the SP (a1, a2 in FIGS. 1B and 1C) to allow the correct flow of the sample and aqueous solutions to the rest of the LFD. The sample application zone can condition the sample, for example by filtering out particulate matter or cells and/or add buffering agents to adjust the pH of the sample, while also ensuring a controlled flow of liquid sample to the rest of the device.

The second zone, which is hereinafter referred to as the conjugate release pad (CRP; c in FIG. 1A), is the next zone to which the sample migrates. In its most common form the CRP contains an analyte-specific binding partner conjugated to a detection moiety, this conjugate hereinafter being referred to as the analyte-specific detection conjugate (ASDC). The ASDC is contained in dried form within the CRP and is dissolved in and migrates with the sample once it comes into contact with it. In sandwich-type assays, the analyte-specific agent is a binding partner which specifically binds to analyte in the sample to form a complex.

The third zone, which is hereinafter referred to as the test zone (d in FIG. 1A), is the next zone contacted by the sample. The test zone usually consists of a nitrocellulose membrane and contains two narrow bands of agent bound to the solid phase and placed at a right angle to the direction of sample flow. The first band, situated closest to the SP and hereinafter referred to as the test band (e in FIG. 1A), consists of another analyte-specific agent, which is immobilized at the site and is hereinafter referred to as the analyte-specific capture agent (ASCA). In sandwich-type assays the ASCA is a binding partner which specifically binds the analyte. When the sample migrates to and through the test band the ASCA binds both free and any ASDC-complexed analyte present, causing an accumulation of both at the test band. If sufficient analyte is present in the sample and if a sufficient proportion is bound to the ASDC, the accumulation of the ASDC at the test band is detected. The second band (f in FIG. 1A) is usually a control band placed downstream to the test band, and may simply consist of an immobilized binding partner specific to the ASDC but not to the analyte. Sufficient build-up of ASDC at the control line indicates the correct passage of the sample though the LFD.

The fourth and final zone with which the sample comes into contact is the absorbance pad (g in FIG. 1A) consisting of an absorbent material which acts to receive the residual sample after it has passed over the test zone, and thus allowing the majority of the sample applied to the LFD to pass through the test zone.

Another LFA format is a competitive-type assay. In competitive-type assays either the ASDC or the ASCA contains the analyte or a derivative of the same instead of an analyte specific binding partner such as is present in sandwich-type assays. In competitive-type assays, analyte present in the sample has a negative influence on the accumulation of ASDC at the test band.

The following description will focus on the phenomena involved with sandwich-type assay formats but the same or similar phenomena also occur in competitive-type assays with changes in the agent to which the phenomena relate. In LFAs the band intensity represents the number of ASDC molecules or particles accumulated at the test band. This number relates to the number of analyte molecules reacted with both the ASCA and ASDC. In order to quantify the analyte in a test sample, the band intensity is compared to that obtained from samples of known analyte content. In a standard LFA, the coefficient of variation is around 20-25% even for a fully optimized assay. An important source of error associated with LFAs is run-to-run variation in the volume of sample exposed to i) the ASDC, and ii) the ASCA, or a combination of the two. These two sources of error will be treated separately in the following, as they result from separate mechanisms and the problems of reducing the variation in each require separate solutions.

i) Variation Associated with Contact between the Analyte and the ASDC

In standard LFAs, the sample is applied to the LFD and migrates from the SP (b in FIG. 1) to the CRP (c in FIG. 1), where it starts to dissolve the ASDC. Once dissolved, the ASDC migrates with the sample to the test zone, at the same time contacting and binding the analyte. Contact between the ASDC and the analyte in the sample depends on the rate of dissolution of ASDC by the sample and the total volume of sample that passes through the CRP. Ideally, the ASDC should be released into the solution evenly over the total sample volume, allowing it to come into contact with all of the analyte distributed in the total sample volume or at least in a constant manner so that the volume of sample contacted is constant. Unfortunately the release rate of ASDC from the CRP can be affected by sample-to-sample and environmental variations. Parameters such as temperature, sample viscosity, sample pH and the ionic strength of the sample may all affect the release of the ASDC from the CRP and therefore the volume of sample contacted.

European patent document EP1716420 and international patent document WO 2006/083367 teach quantitative LFA methods in which the detection conjugate (ASDC) is combined with the sample before it is applied to the LFA device. In this way the conjugate interacts evenly with all of the analyte in the sample, thus overcoming the effect of variation in the CRP release rate.

Multiple-step methods have also been developed in which the ASDC enters into contact with the test band after the analyte present in the sample has been immobilized at the test band by the ASCA. The amount of analyte immobilized relates to the amount of analyte that has entered into contact with the ASCA. The ASDC then enters into contact with the immobilized analyte. Ideally an excess of ASDC contacts with the immobilized analyte, binding to most if not all of the immobilized analyte, so that the response obtained is not affected by the normal test-to-test variations in the amount of ASDC that contacts with the immobilized analyte.

ii) Variation Associated with Contact between the Analyte and the ASCA

The final response in a standard LFA relates to the number analyte molecules that are bound to the ASCA and therefore depends on the amount of sample that comes in contact with the ASCA. Variations in the flow characteristics of the sample through the LFD can affect both the total volume of sample passing through the test band and the proportion of analyte molecules in the sample that contact the ASCA immobilized in the test band. If the sample flow is slower, the analyte molecules have a longer time to diffuse to and interact with the immobilized ASCA molecules as they pass through the test band. This means that the ASCA is able to interact with a higher proportion of the analyte molecules in the sample. However, as the flow rate increases, more sample and therefore more analyte can pass though the test band contacting the ASCA. Factors such as temperature affect both the flow rate of the sample and the diffusion rate of the analyte. Other factors such as sample viscosity and variations in the membrane properties, for example due to differences in the humidity of the atmosphere in which the LFA is run, will all affect on one or both of these properties. As a result it is difficult to predict the effects of between-sample variation and the effects of variation in environmental conditions.

International patent document WO 2006/083367 teaches methods in which errors due to variations in the volume of sample that enters into contact with the ASCA are compensated for by using analyte-independent binding pairs that are not endogenous to the sample, with one of the pair being immobilized at the control band. Variation in the volume of sample contacting the ASCA immobilized at the test band are mirrored in the control band, the signal from which can then be used to correct the reading obtained from the test band.

DEFINITIONS

Terms Used in the Following Description May have Particular Meanings, Defined as follows:

Analyte: the substance, presumed to be present in the sample, which has to be detected or quantified.

Analyte-specific agent: a chemical agent that relates specifically to the analyte in two ways: it may be a molecule or complex or conjugate of molecules that binds specifically to the analyte, or, in competitive-type assays, it may relate specifically to the analyte, by competing with the analyte for binding an analyte specific binding partner, but by being an analogue or derivative of the analyte.

Analyte-specific capture agent (ASCA): An analyte-specific agent which specifically binds to the analyte in sandwich-type assays. It may be immobilized at the test band, or it may contain a moiety which is capable of binding specifically to a test band receptor (TBR) immobilized at the test band.

Component: One part of the liquid, being for example free analyte, QA, DA or DC or a complex between two or more of such.

Detection agent (DA): Any agent used to allow the detection of positive component immobilized at the test band.

Detection conjugate (DC): An detection agent (DA) capable of binding to the positive component either directly or via another DA and containing a detection moiety labeled directly or via labeled particles or microspheres including liposomes, metal colloid or latex (polystyrene) microspheres, the labeling agents including colorimetric, fluorescent, luminescent, magnetic, paramagnetic or other appropriate labels.

Generic lateral flow device (gLFA): A lateral flow device in which the test band receptor (TBR) does not specifically bind to the analyte of interest or to analyte specific binding partner located within the LFD.

Negative component: A component present in or formed in the mixture of sample with analyte-specific agents which binds to the test band receptor (TBR) but produces no signal because it is not labeled and does not combine with a DA or DC.

Positive component: A component present in or formed in the mixture of sample with analyte-specific agents which binds to the test band receptor (TBR) and produces a positive signal either through being labeled itself or by combining with a DA or DC.

Quantification agent (QA), agent or component: an analyte-specific agent that is essential for the quantification of the analyte in the LFA procedure. If it is an analyte-specific agent that binds specifically to the analyte it has a heterobifunctional specificity, so that it is also capable of binding specifically to the test band receptor (TBR), or detection agent (DA) or (DC). If it is an analogue or derivative of the analyte, it may be capable of binding specifically to the TBR and, if it is not itself labeled, to a labeled DA or DC. It may also be a labeled DA or DC capable of binding to the analyte or to an analyte-specific agent.

Quantification ratio (QR): The ratio between the positive and negative components in sample mixture which are capable of binding to the test band receptor (TBR).

Sample mixture: The mixture formed by adding a known amount of analyte-specific agents, including quantification agents (QAs), to a known amount of sample before the mixture is applied to the LFD.

Sufficient excess: The amount of test band receptor (TBR) binding QA required to sufficiently saturate the TBR immobilized at the test band Sufficient saturation of the immobilized binding partner or test band receptor: That degree of saturation of the test band receptor (TBR) which produces the desired precision of quantification on completing the quantification procedure. The use of an excess of an agent to saturate or near-saturate its binding partner is a common aspect of many analytical technologies known to prior art. In the present disclosure, it allows for the amount of the analyte-specific TBR binding partner immobilized at the test band to be independent of the expected test-to-test variation in the amount of sample contacting the test band. The relationship between the amount of sample contacting the test band and the amount of TBR binding partner immobilized is hyperbolic in nature. Initially, the amount of the TBR binding partner immobilized at the test band is nearly linearly dependent on the amount of liquid contacted. As more liquid passes over the test band, a higher proportion of the TBR molecules form a complex with their binding partner and are no longer available for further binding. As fewer TBR molecules become available, the binding rate decreases until a point is reached where the amount of TBR binding partner immobilized at the test band does not increase with further contact with the solution. This point is defined as the saturation point, and at that point the TBR is defined as being saturated. When an LFA is developed, a set of criteria is defined which includes the required precision of the LFA, sample variability and the conditions under which the test is to be carried out. To achieve the required precision, it may not be necessary to fully saturate the TBR. The amount of the TBR binding partner is adjusted to keep the precision of the assay within that required over the required range of samples and conditions, and this amount of TBR binding partner is defined as sufficiently saturating the TBR.

Test band receptor (TBR): Also referred to as the immobilized binding partner in the test band of an analyte-specific agent. It is a substance immobilized in the test band which is capable of specifically capturing an analyte-specific agent, whether or not complexed with analyte, at the test band.

SUMMARY OF THE INVENTION

The present invention comprises a method of quantification of an analyte, A, in a test sample by means of a single immunochromatographic device, such as a lateral flow device (LFD), comprising: a) mixing a determined amount of said test sample with a determined amount of a quantification agent, QA1, said QA1 being capable of binding specifically and simultaneously both to an immobilized binding partner and to A, thus obtaining a mixture wherein the amount of A in said test sample is reflected by the ratio of the concentration of A-QA1 complex formed to the concentration of free QA1 in said mixture; b) applying a determined volume of said mixture to said device equipped with a test band in which said binding partner of the QA1 is immobilized, so that A-QA1 complex and free QA1 are immobilized at said test band in a ratio that relates to their concentration ratio in the mixture applied, said volume of mixture being determined to provide a total amount of A-QA1 complex and free QA1 capable of sufficiently saturating the immobilized binding partner in said test band; c) measuring the amount of either said A-QA1 complex or free QA1 immobilized at the test band by means of an appropriately chosen detection procedure; and d) comparing the result obtained from the test sample with the results obtained from calibration samples containing known or allocated amounts of A and thus determining the amount of A in said test sample.

Alternatively, said method comprises a method of quantification of an analyte A, in a test sample by means of a single immunochromatographic device, such as a lateral flow device (LFD), comprising the steps of: a) mixing a determined amount of said test sample with a determined amount of a quantification agent, QA2, said QA2 being an analogue or derivative of A which is capable of binding specifically and simultaneously both to an immobilized binding partner and to another quantification agent, QA3, said QA3 being capable of binding specifically both to QA2 and A, thus obtaining a mixture wherein the amount of A in said test sample is reflected by the ratio of the concentration of QA3-QA2 complex formed to the concentration of free QA2 in said mixture; b) applying a determined volume of said mixture to said device equipped with a test band in which said binding partner of the QA2 is immobilized, so that QA3-QA2 complex and free QA2 are immobilized at said test band in a ratio that relates to their concentration ratio in the mixture applied, said volume of mixture being determined to provide a total amount of QA3-QA2 complex and free QA2 capable of sufficiently saturating the immobilized binding partner in said test band; c) measuring the amount of either said QA3-QA2 complex or free QA2 immobilized at said test band by means of an appropriately chosen detection procedure; and d) comparing the result obtained from said test sample with the results obtained from calibration samples containing known or allocated amounts of A and thus determining the amount of A in said test sample. In one embodiment the amount of QA3-QA2 complex immobilized at said test band is measured by contacting with a detection agent (DA3) capable of binding specifically to QA3 in said QA3-QA2 complex. In one embodiment the amount of free QA2 immobilized at said test band is measured by contacting with a detection agent (DA4) capable of binding specifically to said free QA2 and not to said QA3-QA2 complex. In another embodiment, said QA3 is labeled directly or via labeled particles or microspheres including liposomes, metal colloid or latex (polystyrene) microspheres, the labeling agents including colorimetric, fluorescent, luminescent, magnetic, paramagnetic or other appropriate labels.

The first procedural stage involves the establishment of a quantification ratio (QR) by mixing a determined amount of sample with a determined amount or amounts of one or more quantification agents (QAs) in one or more steps, so that the analyte (A) in the sample is in uniform contact with the QA or QAs and the amount of A in the sample is reflected by proportions of components of the mixture resulting from the binding of a QA to the analyte in the sample or possibly another QA added at a separate step. This procedure is applicable to both sandwich-type assays and competitive-type assays. In sandwich-type assays a single QA1 binds specifically to A to form a complex, whereby the QR is defined as the proportion between the amount of the free QA1 and the QA1-A complex in the resultant sample mixture. In competitive-type assays, a QA2 being an analogue or derivative of A is added to the sample at a step before or after the addition of QA3 which binds specifically and not concurrently to A and QA2 whereby the resultant QR can be defined as the proportion between free QA2 and QA2-QA3 complex or free QA3 to QA2-QA3 complex.

The second procedural step relates to applying a determined volume of said mixture to an LFD equipped with a test band in which a binding partner to one said QAs is immobilized, so that two of the said components of the mixture are immobilized at the test band in a ratio that relates to their proportional concentration in the mixture applied, said volume of mixture being determined to provide a total amount of said components capable of producing sufficient saturation of the immobilized binding partner in the test band.

The quantification procedure is completed by a third and fourth procedural stage. The third stage comprises measuring the amount of one or more of said components immobilized at the test band by means of an appropriately chosen detection procedure. The fourth procedural stage comprises comparing the result obtained from the test sample with the results obtained from calibration samples containing known or allocated amounts of A and thus determining the amount of A in the test sample.

By including the two procedural stages a) and b) this greatly diminish or eliminate the sources of run-to-run variation described above.

An advantage of the described procedure consists in eliminating variation in the contact between sample and quantification agents by mixing the sample with analyte-specific agents to provide uniform contact under quantitatively controlled conditions, diminishing or eliminating the effects of variation in sample viscosity and run temperature by applying an amount of sample mixture that is known to produce sufficient saturation of the test band receptor to ensure the required assay precision, and, by appropriate choice of the functionality of the analyte-specific agents and the test band receptor, enabling the production of a generic LFD (gLFD) that is capable of quantifying a large number of different analytes.

DETAILED DESCRIPTION OF THE INVENTION

This invention relates to methods for enabling a reduction in errors due to variations associated with the contact between the sample and the test band, for use in association with established methods that overcome the variations in contact between the sample and the ASDC. The invention relates to the combination of the following three aspects in an LFA method:

i) The receptor immobilized at the test band is not specific to the analyte but binds an analyte-specific agent which is either a specific binding partner of the analyte or a derivative or analogue of the analyte.

ii) A defined amount of analyte-specific agent is contacted with a defined amount of sample and possibly with other agents, before the resultant sample mixture is applied to the LFD.

iii) A sufficient excess of the analyte-specific agent is contacted with the test band receptor, so that test-to-test variations in the amount of sample contacting the test band do not affect the resultant amount of the analyte-specific agent immobilized at the test band.

The combination of all three aspects in an LFA method allows for the development and production of quantitative LFAs with a higher precision and reduced development costs, as it only requires the detection of a single label and allows the use of generic lateral flow devices (gLFD) that can be used to quantify a large number of different analytes.

Using a test band receptor (TBR) that is not specific to the analyte itself has a number of advantages. The TBR can be chosen or designed to bind and immobilize any one of variety of agents that are individually specific to different analytes. In one non-limiting example, the TBR can be a biotin-binding molecule (for example, avidin, neutravidin, streptavidin or any analogue or derivative of these) and the analyte-specific agent is conjugated with biotin, thus allowing, for example, the use of antibodies that are individually specific to any number of analytes, said antibodies being conjugated with biotin by standard methods known to those skilled in the art.

The use of a TBR that is not specific to the analyte but reacts specifically with an analyte-specific binding partner present within the LFD is taught in prior art. The analyte-specific binding partner combines with the sample, allowing the analyte in the sample and the specific binding partner to react before migrating to the test band. U.S. patent document U.S. Pat. No. 4,861,711 discloses methods of quantifying an analyte in a sample by using a sheet-like test device in which all the analyte-specific and other agents are situated at defined regions within the device. Sample or sample diluted in a buffer or water is added to the device via an application site, from which it migrates to and dissolves dried agents in the device, allowing various binding pair interactions to occur. Further application sites allow the addition of buffer or water to dissolve other dried agents, which then migrate to and react with the analyte or other agents located on the device. International patent documents WO97/06439, WO00157522 disclose how an analyte-specific binding partner can be located close to or within the sample pad, being able to interact with the analyte from the time when the sample is applied to the sample pad to when the analyte-specific binding partner passes the TBR, to which it can also bind. This procedure was found to increase the sensitivity of the LFA by providing a much longer period of interaction than when the analyte-specific binding partner is immobilized at the test band. In the above two disclosures, the sample is mixed with the analyte-specific agent in a dynamic situation in which the analyte-specific agent is being dissolved by the sample at the same time as some of the sample is migrating through the test device, so that it is not possible to obtain a controlled mixing of the analyte and the agent. In addition, both of above disclosures employ analyte-specific agents which are included within the test device, so that such a device would not be usable as a gLFD.

A number of methods that relate to the production of a gLFD are known to prior art. International patent document WO02083894 discloses the use of complementary pairs of linear nucleic acid sequences to provide the analyte-independent binding of an analyte-specific agent to the TBR. One linear nucleic acid sequence is the TRB, being immobilized at the test band, while the complementary nucleic acid sequence is conjugated to the analyte-specific agent. The document teaches that this technology could be used to produce a gLFD, but does not disclose methods of improving quantification. International patent document WO 2007/011936 teaches methods to improve the quantification of LFAs relating to gLFDs and discloses two separate detection labels. An analyte-specific binding partner is immobilized to magnetic beads which also contain the first detection label, the sample being contacted with the magnetic beads before application to the LFD. The analyte in the sample contacts and binds to the magnetic beads. The magnetic beads are immobilized at the test band by a magnetic field as the sample passes through the device. Analyte immobilized at the test band is detected by means of an analyte-specific binding partner conjugated to a second label distinguishable from that present on the immobilized magnetic beads. The amounts of magnetic beads and detection conjugate immobilized at the test band are detected by separate reader systems. The response obtained from the first label is used to compensate for test-to-test variation in the amount of sample contacting the test band, while the response obtained for the second label relates to the amount of analyte present at the test band.

Prior to the application of sample to the LFD, it can be contacted with various analyte-specific agents in a controllable and definable manner. However, once the sample applied to the LFD, the contact between the sample and the TBR is much less controllable. There are many factors that can affect the flow characteristics of the sample through the LFD. Both test-to-test variations such as temperature or sample viscosity and LFD-to-LFD variations can have a marked effect on the volume of sample that contacts the TBR. It is possible to compensate for these variations as disclosed by patent documents WO 2006/083367 and WO 2007/011936. However, the present disclosure outlines how it is also possible to use the TBR in such a way as to make the resultant response independent of these variations. The use of an excess of an agent to saturate or near-saturate its binding partner is a common aspect of many analytical technologies known to prior art. In the present disclosure, it allows for the amount of the analyte-specific TBR binding partner immobilized at the test band to be independent of the expected test-to-test variation in the amount of sample contacting the test band. The relationship between the amount of sample contacting the test band and the amount of TBR binding partner immobilized is hyperbolic in nature. Initially, the amount of the TBR binding partner immobilized at the test band is nearly linearly dependent on the amount of liquid contacted. As more liquid passes over the test band, a higher proportion of the TBR molecules form a complex with their binding partner and are no longer available for further binding. As fewer TBR molecules become available, the binding rate decreases until a point is reached where the amount of TBR binding partner immobilized at the test band does not increase with further contact with the solution. This point is defined as the saturation point, and at that point the TBR is defined as being saturated. When an LFA is developed, a set of criteria is defined which includes the required precision of the LFA, sample variability and the conditions under which the test is to be carried out. To achieve the required precision, it may not be necessary to fully saturate the TBR. The amount of the TBR binding partner is adjusted to keep the precision of the assay within that required over the required range of samples and conditions, and this amount of TBR binding partner produces sufficient saturation of the TBR to obtain the required precision.

There is a large variety of possible general methods and formats that can be developed within the three aspects of this invention. Most importantly, the ratios between the various analyte-specific components are defined in the sample before it is applied to the device. The analyte-specific agents can be analyte binding partners or derivatives or analogues of the analyte. The analyte-specific components can be i) the analyte in complex with an analyte-specific binding partner, ii) free analyte-specific agents, or iii) a complex between an analyte-specific binding partner and analyte analogue or derivative. This invention not limited to any particular method of improving the contact between detection agents (DA) and/or detection conjugate (DC) and the sample, and can make use of various methods that do so. A component is considered to give a positive result if the relevant binding partner to a DA or DC is immobilized at the test band. In most cases sufficient DC and possibly DA will be used to saturate the binding partner accumulated at the test band. If DC or DA is added to the sample before it is applied to the device, its concentration should also be constant. In this way, even if the binding partner in the resultant mixture is not saturated, then the proportion of bound to non-bound binding partner will be constant for that binding partner concentration.

The mixing of a determined amount of the sample with a determined amount of one or more analyte-specific agents results in a number of components including free analyte and agents as well as complexes between them. Components are considered positive if they are capable of binding to the TBR, thus allowing the immobilization of the DC at the test band. Components that bind to the TBR and do not allow the immobilization of the DC at the test band are considered as negative. The quantification ratio (QR) is defined as the ratio between the concentrations of the positive and negative components, the QR being related to the concentration of analyte in the original sample. By sufficiently saturating the TBR, the combined amount of both the negative and positive components immobilized at the test band can be made suitably independent of the variation in the volume of sample mixture that contacts the test band. The ratio of the positive and negative components immobilized at the test band relate to those found in the sample mixture. In this way, the amount of positive component immobilized at the test band relates to the concentration or amount of analyte in the sample in a manner that is independent of variation in the amount of sample that contacts the test band.

The positive component can be detected directly or via use of a detection conjugate (DC) resulting in a complex between the relevant component and a detection moiety labeled directly or via labeled particles or microspheres, including liposomes, metal colloid or latex (polystyrene), labeling agents including colorimetric, fluorescent, luminescent, magnetic, paramagnetic or other appropriate labels. A detection agent (DA) may also be used where the DC does not bind directly to the positive component, the DA being capable of binding both the positive component immobilized at the test band and the DC. Contact between the DA, DC and the components relevant to the QR can be achieved before or after the relevant QR components are immobilized at the test band.

The basis and practice of the invention are illustrated by the following non-limiting examples:

EXAMPLE 1

Saturating the Test Band Receptor (TBR)

This illustrates how varying the concentration of the QA responsible for binding the TBR affects the dependency of signal on the volume of sample seen by the TBR. The quantification agent (QA) is biotinylated tetanus toxoid (TT-B)

prepared by standard laboratory techniques. The analyte (A) is the mouse monoclonal antibody HYB 278-10 against tetanus toxoid, supplied by AntibodyShop, Denmark. The detection conjugate (DC) is a goat antibody to Fc fragment of mouse IgG, conjugated to 25 nm gold colloid supplied by Dima, Germany. The running buffer is standard phosphate-buffered saline (PBS) containing 0.5% w/v bovine albumin and 0.05% v/v Tween-20. The lateral flow device (LFD) consists of the test strip sandwiched between the upper lower halves of the device housing supplied by Reagena, Finland, the upper half containing two application wells. The test strip consists of a sample application pad supplied by Advanced Microdevices, India, analytical membrane supplied by Millipore, USA, and an absorption pad supplied by Whatman, England. The analytical membrane contains a test band made by applying a test band receptor (TBR) consisting of neutravidin (Pierce, USA) 1 mg/ml in PBS and a control band made by applying a 0.5 mg/ml solution of donkey antibody against goat IgG (Dima, Germany) in PBS.

Serial doubling dilutions of QA in running buffer were made from 20 µg/ml to 0.039 µg/ml. 100 µl of each QA solution were added to separate tubes containing 100 µl of A at 1 µg/ml and DC (OD 0.4 at 540 nm) in running buffer. The tubes were vortex-mixed for 30 seconds and allowed to equilibrate for 5 minutes before applying 150 µl of the mixture to the application well of the LFD (see FIG. 1C, a2). Readings were then taken after 5, 10 and 15 minutes using a prototype DiaScan 10 hand-held reflectometer (Otsuka Electronics, Japan), which displayed the responses for the control and test bands, with a reference value taken from the region between these bands.

Once mixed, the QA and A form a complex, but free QA and A are still present in the mixture. The relative ratios of these components relate to the concentrations of the A and QA in the original solutions. The QA also binds to the TBR and is immobilized at the test band when contacted by the sample mixture. The concentration of A is kept constant from sample to sample. The quantification ratio (QR) is the ratio of concentrations of QA bound to A (giving a positive result) to QA not bound to A (giving a negative result).

In this example, the DC is included in the sample mixture when applied to the LFD. The amount of DC added to each sample is also kept constant and ideally should be sufficient to saturate the analyte A in the sample, but even if this is not the case, the constant amount of DC ensures that the ratio of DC-bound A to non-DC-bound A will be constant for a given concentration of A. So for any concentration of A, a set proportion of A immobilized at the test line will be in complex with the DC.

The aim of the experiment was to define the concentration of QA, at which the TBR becomes sufficiently saturated after 10 minutes, so that the resultant signal is independent of the expected variations in the volume of sample seen by the TBR. The samples had the same viscosity and the tests were carried out at 22° C., but the usual LFD-to-LFD variations due to other factors were expected.

Figure 2:
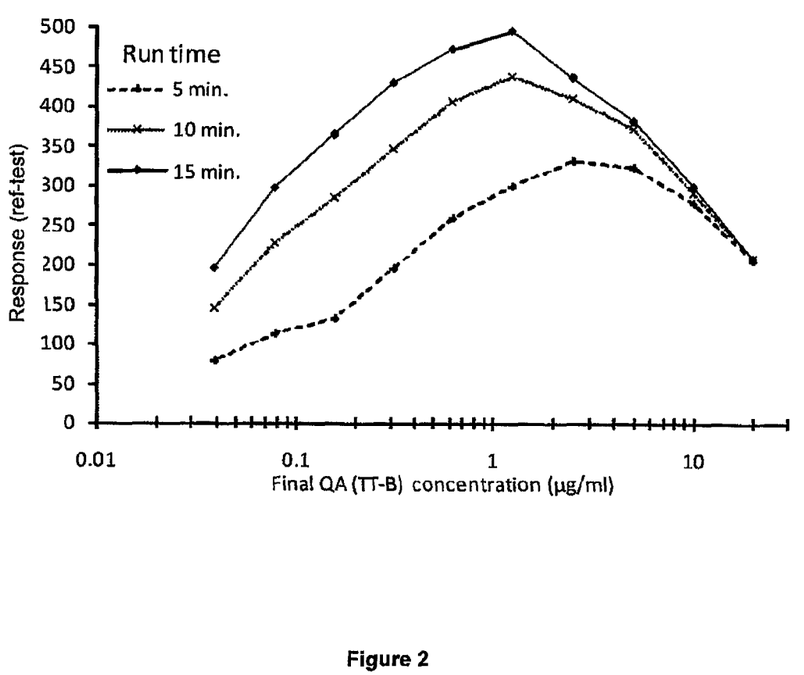
FIG. 2 shows graph of LFA responses (reflectance reference value minus test band value) for illustration of Example 1.

The results are shown in FIG. 2. At the lower QA concentrations the QA was unable to saturate the TBR and there was an increase in the response as more of the sample mixture came in contact with the TRB between the readings at 10 and 15 minutes. With an increase in the QA concentration, this difference decreased as the TBR became more saturated. At a QA concentration of 5.0 mg/ml there was little or no difference in the responses at 10 and 15 minutes. This QA concentration would therefore be expected to be suitable for a 15-minute assay. At a QA concentration of 10 µg/ml the TBR was almost completely saturated even after 5 minutes, and would be expected to be sufficiently saturated so that the response would be suitably independent of the expected variations in the volume of sample seen by the TBR. At a QA concentration of 20 µg/ml the TBR was saturated even earlier and appeared to be fully saturated after 5 minutes, so that the test could be read from 5 to 15 minutes after the sample had applied to the LFD without a significant change in the result obtained.

EXAMPLE 2

Minimizing the Effect of Sample Viscosity by Saturating the TBR

This illustrates how effects due changes in sample viscosity can be minimized when saturating the TBR. Two QA concentrations that gave a similar response after a run time of 10 minutes in Example 1 were used. As the response is the same the same amount of complex is immobilized at the test line. However, at the lower QA concentration (0.2 µg/ml) the response was dependent on the amount of A-QA complex that came into contact with the TBR. At the higher QA concentration (10 µg/ml) the TBR was saturated and the response relates to the concentration ratio of A-QA complex to free QA in the sample contacting the TBR. Unless otherwise stated, the protocol, materials, reagents and concentrations were the same as those outlined in Example 1. The control runs used standard running buffer, whereas test runs simulated the effect of an increase in sample viscosity by adding 10% v/v glycerol to the running buffer. All results were determined after a run time of 10 minutes.

Figure 3:
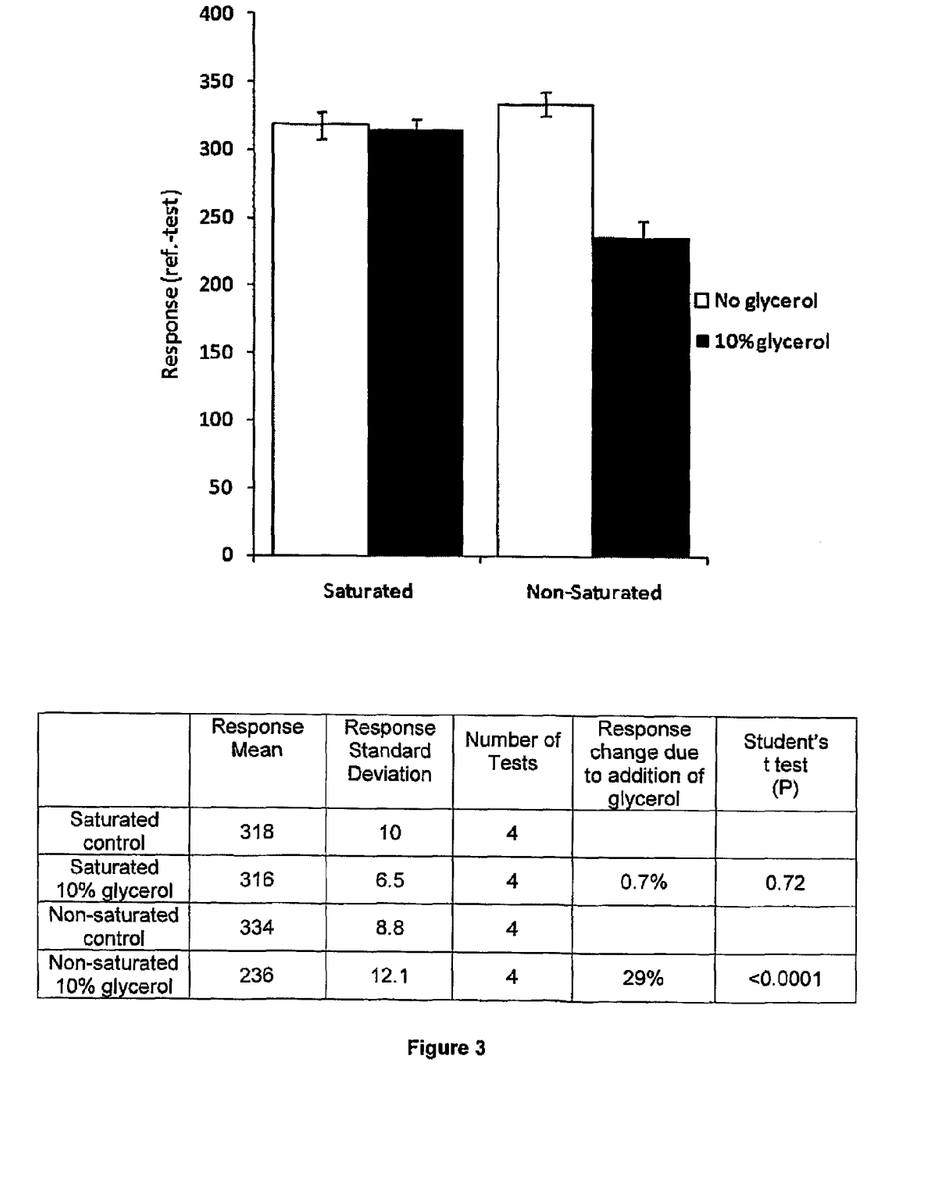
FIG. 3 shows bar diagram and table of LFA responses for illustration of Example 2, showing the effect of a change in viscosity of the sample mixture on the responses obtained when the test band receptor is saturated and when its not saturated.

The results are shown in FIG. 3. The addition of glycerol to the sample mixture markedly reduced its flow through the LFD, as was apparent from the amount of sample still present in the application well after 10 minutes. The reduced amount of sample mixture coming in contact with the TBR had a marked effect on the response obtained at the lower QA concentration, the response falling by 29% in the presence of glycerol. In contrast, there was no significant fall in the response in the presence of glycerol when the higher QA concentration was used to ensure saturation of the TBR.

EXAMPLE 3

Minimizing the Effect of Run Temperature by Saturating the TBR

Temperature can also have a marked effect on the flow characteristics of an LFA. This example illustrates how saturating the TBR helps overcome the variations in response due to differences in run temperature. The protocol, materials and reagents are the same as those outlined for the control runs of Example 2. Three runs were performed at each of three different ambient temperatures, 12° C., 22° C. and 37° C.

Figure 4:
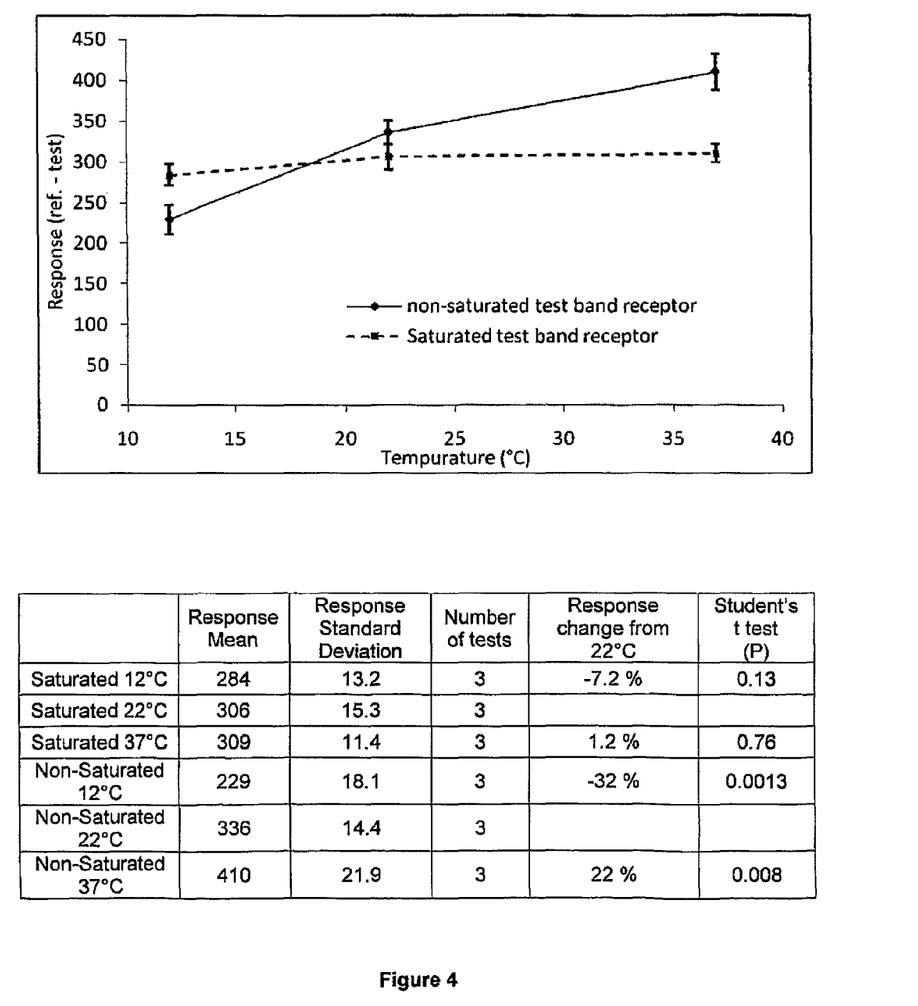
FIG. 4 shows graph and table of LFA responses for illustration of Example 3, showing the effect of changes in run temperature on the responses obtained when the test band receptor is saturated, and when it is not saturated.

The results are shown in FIG. 4. The run temperature was found to have a marked effect on the running of the sample mixture through the LFD. At 12° C., a marked amount of sample mixture remained in the sample application well after 10 minutes, indicating a reduction in the amount of mixture that had come into contact with the TBR. A significant fall (−32%) in the response compared with that at 22° C. was obtained at the lower, non-saturating QA concentration. A fall in response was also evident with the higher QA concentration, indicating that the TBR was not totally saturated within 10 minutes. However this fall in response was much less (−7.8%) than at the lower QA concentration. At 37° C. the flow rate of the sample mixture through the LFD appeared to increase. The runs at the lower, non-saturating QA concentration showed a marked increase in the signal obtained (22%) compared with that at 22° C., consistent with an increase in the amount of sample mixture that had come into contact with the TBR. The response obtained with the runs at the higher QA concentration remained effectively constant in comparison with that at 22° C., showing an increase of only 1.2%. If required, the 7.8% fall in response obtained for the runs with higher QA concentration at 12° C. could be reduced by either increasing the QA concentration, for example to 20 µg/ml, or by increasing the run time, for example to 15 minutes, with a view to obtaining sufficient saturation of the TBR. The appropriate parameters would be defined during the development of the LFA.

EXAMPLE 4

Standard Curve Obtained

This example illustrates how the present invention can be used to produce a quantitative LFA. Unless otherwise stated the materials and reagents used are the same as those outlined in Examples 1-3. The quantification agent solution contained QA at 20 µg/ml and DC (OD 0.4 at 540 nm) in running buffer. Standards were made from a 1 mg/ml stock solution of A, with serial doubling dilutions from 1000 to 31.25 ng/ml in running buffer. Each standard was tested in triplicate. 100 µl of the quantification solution was mixed with 100 µl of the relevant standard and allowed to equilibrate for 5 minutes before applying 150 µl of the mixture to the application well of the LFD.

Figure 5:
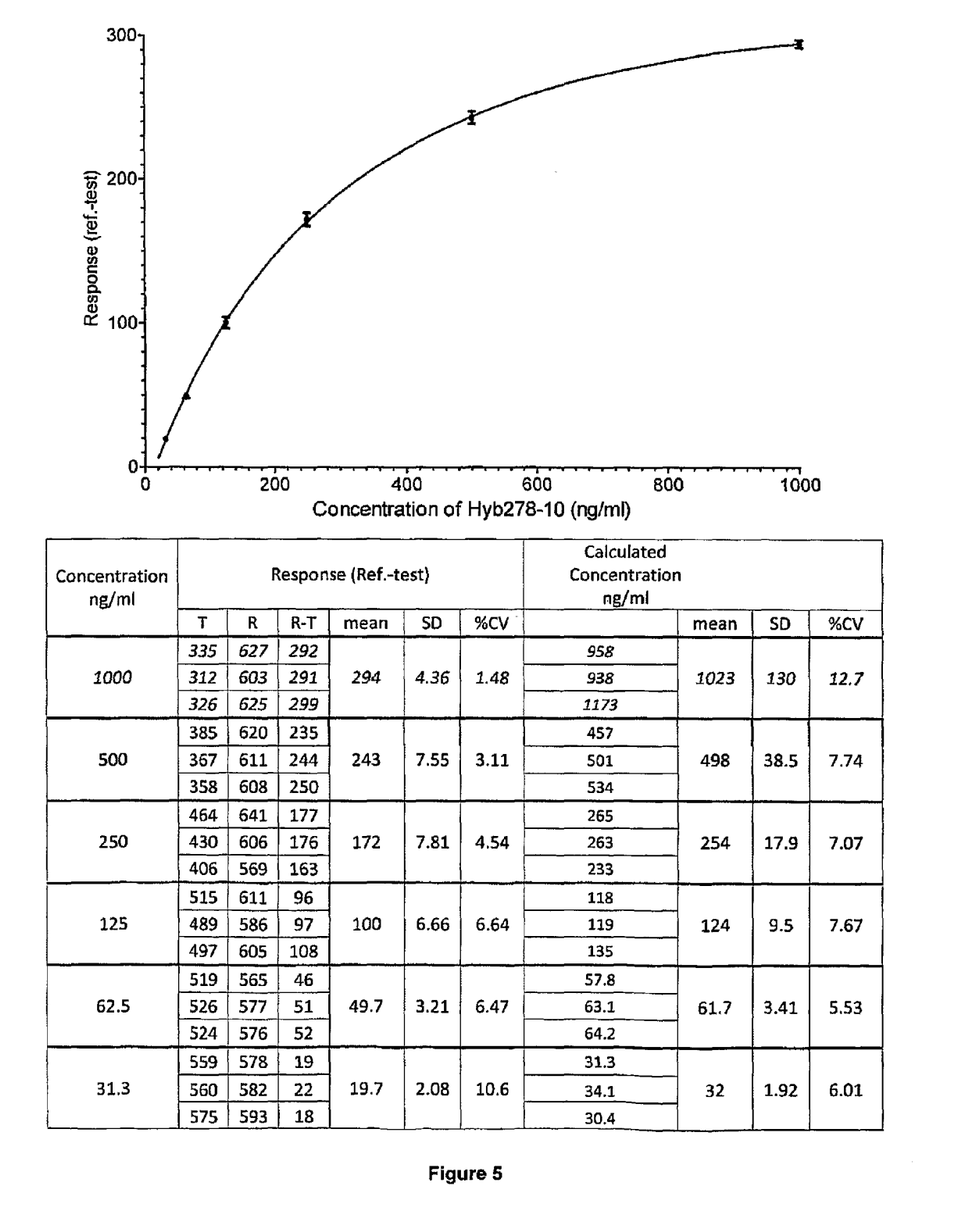
FIG. 5 shows standard curve and table of LFA responses for illustration of Example 4, showing the values obtained for analyte (Hyb 278-10) concentrations ranging from 31.3 ng/ml to 1000 ng/ml.

The results are shown in FIG. 5, which demonstrates the precision of this test over the range of the standard curve. At an analyte concentration above 500 ng/ml the response curve flattens off to such a degree as to not permit a precise concentration determination. Response values correlating to an analyte concentrations above 500 ng/ml indicate that the sample should be further diluted by a factor of two and retested. Over the range of 500 ng/ml to 62.5 ng/ml the test gave coefficient of variance (CV) values for the calculated concentrations ranging from 5.5% to 7.7%, which are comparable with those obtained with ELISA.

EXAMPLE 5

Different Analyte and Assay Format Using the Same LFD

This illustrates another advantage of the present invention: that the same LFD can be used to develop assays for different analytes and with different assay formats. This permits the production of a generic LFD that can be used by different operators to develop different LFAs without having to invest in specific equipment and expertise to produce their own specific LFD. This example illustrates a two-step assay to determine mouse IgG1 (mIgG1) concentrations in hybridoma culture supernatant samples. The method was developed using the same LFD and DC as in Examples 1-4. Mouse IgG1 (Sigma-Aldrich, USA) was used to produce the calibrators based on the concentration of the stock solution stated by the supplier. In the final assay, the culture supernatant sample is first diluted 1/20 to allow the expected analyte levels to fall within the assay range. The QA is biotinylated goat anti-mouse IgG (Fab fragment) supplied by Sigma-Aldrich, USA and is used at a concentration of 20 µg/ml in running buffer. The DC solution, which is separate, contains DC in running buffer at a concentration giving OD 0.6 at 540 nm. 20 µl of the QA solution are added to 20 µl of the calibrator or diluted sample and mixed. The analyte A and QA form a complex, but free A and QA are still present in the sample mixture. The proportional concentrations of these three components relate to the concentrations of A and QA in the original solutions. As the QA is biotinylated it binds to the TBR (neutravidin). The concentration of the QA is kept constant from sample to sample. In this example the quantification ratio (QR) is the ratio of QA bound to A (A-QA, which is the positive component) to free QA (QA not bound to A, which is the negative component). Once the sample mixture has equilibrated for 5 minutes, 20 µl of the mixture are applied to the sample application well (FIG. 1C a1) of the LFD. This is followed by 150 µl of DC solution applied to the upstream application well (FIG. 1C a2). The DC solution flows through the LFD pushing the sample mixture in front of it. As the sample mixture passes over the test zone, the free QA and analyte-complexed QA (A-QA) are captured and immobilized by the TBR. This technology relies on the fact that device-to-device variation in the amount of active TBR is relatively small and that there is an adequate concentration of QA in the sample mixture to sufficiently saturate the TBR. In this way, variations in the amount of sample mixture contacting the TBR do not significantly affect the total amount of QA bound at the test band. The ratio of free QA to A-QA immobilized at the test band must also relate to the concentration of A in the sample. If this is the case, then the amount of A-QA immobilized at the test band closely relates to the concentration of A in the sample. The amount of A immobilized at the test band as A-QA is then detected by the DC, which in this test binds to A and is immobilized by the A in A-QA immobilized at the test band. Thus the amount of DC immobilized relates to the concentration of A in the sample.

Figure 6:
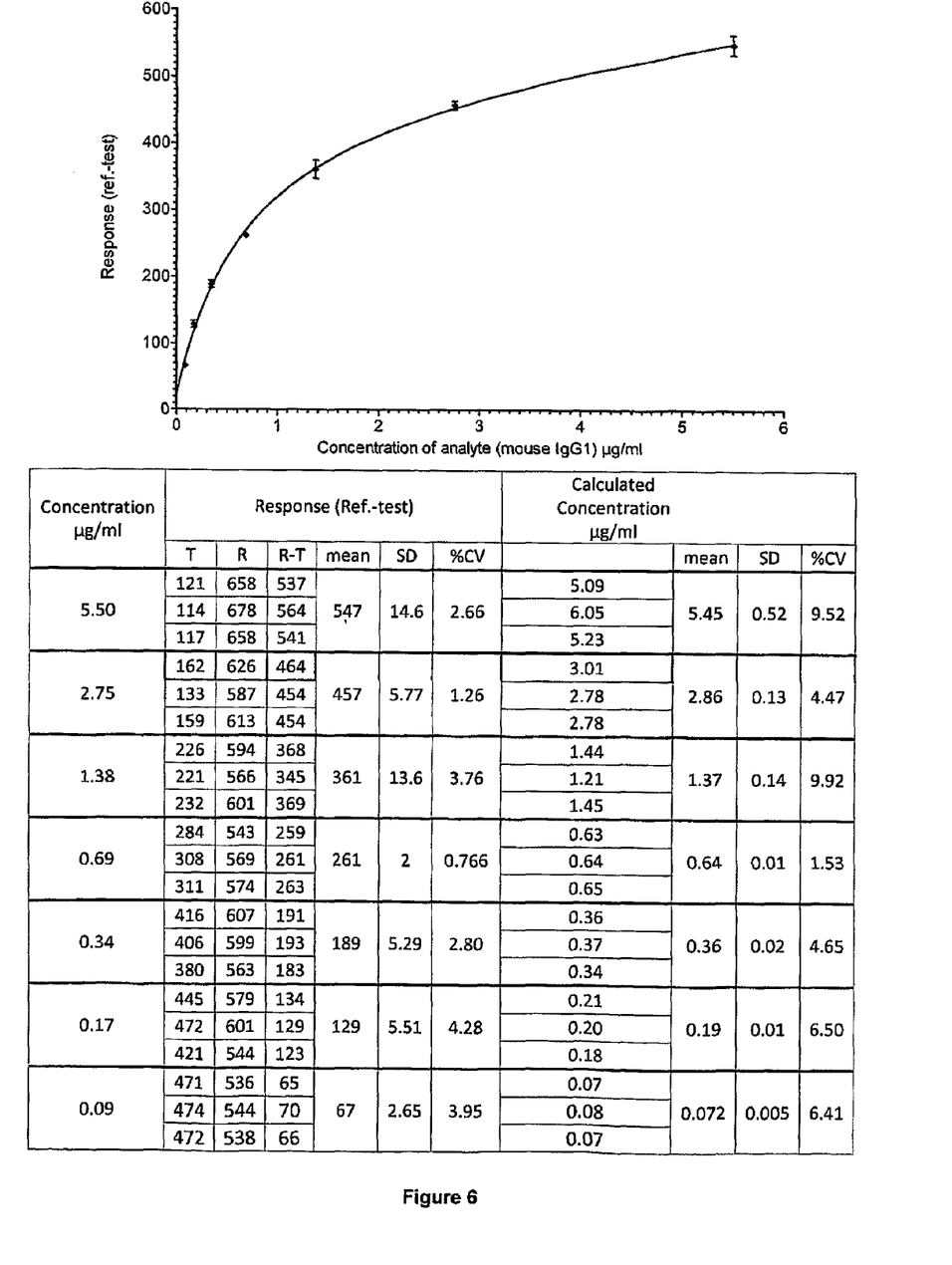
FIG. 6 shows standard curve and table of LFA responses for illustration of Example 5, showing the values obtained for analyte (mouse IgG1) concentrations ranging from 0.09 µg/ml to 5.5 µg/ml.

The results are shown in FIG. 6, demonstrating the precision of this test over the range of the standard curve. Over an analyte concentration range of 0.09 µg/ml to 5.5 µg/ml the test gave coefficient of variance (CV) values for the calculated concentrations from 1.5% to 9.9%, the upper value of which is higher than the CV range of Example 4, but the CV range is still comparable with that obtained with ELISA. This example demonstrates how one LFD can be used to produce LFAs for different analytes and using different detection methods.

Figure 1:
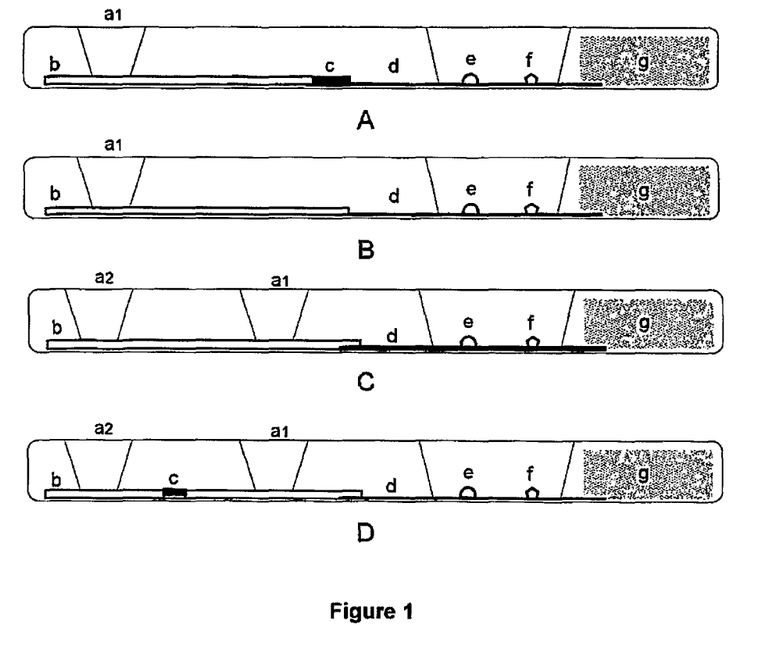
FIG. 1 shows schematic sections of four different types of LFD: (A) a common lateral flow device, (B) a common lateral flow device without a conjugate release pad, (C) a lateral flow device with two application wells, and (D) a lateral flow device with two application wells and a conjugate release pad located between the two wells.

FIG. 1: Schematic sagittal sections of (A) a common lateral flow device, (B) a common lateral flow device without a conjugate release pad, (C) a lateral flow device with two application wells, and (D) a lateral flow device with two application wells and a conjugate release pad located between the two wells. The lateral flow devices containing the following structures, positioned as shown in the sections: a first application well (a1), a second application well (a2), the sample pad (b), detection conjugate contained in a separate conjugate release pad or within the sample pad (c), test zone membrane (d), test band (e), control band (f), and absorption pad (g).

FIG. 2: Graph of LFA responses (reflectance reference value minus test band value) obtained in Example 1, showing values obtained after running for 5, 10 and 15 minutes with a range of quantification agent (QA; biotinylated tetanus toxoid, TT-B) final concentrations from 0.039 µg/ml to 20 µg/ml.

FIG. 3: Bar diagram and Table of LFA responses obtained in Example 2, showing the effect of a change in viscosity of the sample mixture on the responses obtained when the test band receptor is saturated by using a quantification agent (QA; biotinylated tetanus toxoid, TT-B) concentration of 10 µg/ml, and when the test band receptor is not saturated when using a QA concentration of 0.2 µg/ml. The viscosity of the sample mixture was increased by adding glycerol 10% v/v to the running buffer. Error bars indicate one standard deviation.

FIG. 4: Graph and Table of LFA responses obtained in Example 3, showing the effect of changes in run temperature on the responses obtained when the test band receptor is saturated by using a quantification agent (QA) concentration of 10 µg/ml, and when the test band receptor is not saturated when using a QA concentration of 0.2 µg/ml. Error bars indicate one standard deviation.

FIG. 5: Standard curve and Table of LFA responses obtained in Example 4, showing the values obtained for analyte (Hyb 278-10) concentrations ranging from 31.3 ng/ml to 1000 ng/ml. The quantification agent (QA) was biotinylated tetanus toxoid (TT-B) at a final concentration of 10 µg/ml. The mean, standard deviation and coefficient of variance at each analyte concentration are given as well as the analyte concentrations calculated from the standard curve fitted using a one site—fit total and non-specific binding equation with GraphPad prism (USA) software. Error bars indicate one standard deviation.

FIG. 6: Standard curve and Table of LFA responses obtained in Example 5, showing the values obtained for analyte (mouse IgG1) concentrations ranging from 0.09 µg/ml to 5.5 µg/ml. The quantification agent (QA) was biotinylated goat anti-mouse IgG antibody at a final concentration of 10 µg/ml. The mean, standard deviation and coefficient of variance at each analyte concentration are given as well as the analyte concentrations calculated from the standard curve fitted using a one site—fit total and non-specific binding equation with GraphPad prism (USA), software. Error bars indicate one standard deviation.

The invention claimed is:

1. A method of quantification of an analyte, A, in a test sample by means of a single lateral flow immunochromatographic device, comprising the steps of:
    a) mixing a determined amount of said test sample with a determined amount of a quantification agent, (QA1), said QA1 being capable of binding specifically and simultaneously both to an immobilized binding partner (BP) and to A, thus obtaining a mixture wherein the amount of A in said test sample is reflected by the ratio of the concentration of A-QA1 complex formed to the concentration of free QA1 in said mixture;
    b) applying a determined volume of said mixture to said device equipped with a test band in which said binding partner (BP) of the QA1 is immobilized, so that A-QA1 complex and free QA1 are immobilized at said test band in a ratio that relates to their concentration ratio in the mixture applied, said volume of mixture being determined to provide a total amount of A-QA1 complex and free QA1 that saturates binding at the immobilized binding partner (BP) in said test band;
    c) measuring the amount of said A-QA1 complex immobilized at the test band; and
    d) comparing the result obtained from the test sample with the results obtained from calibration samples containing known or allocated amounts of A and thus determining the amount of A in said test sample.

2. A method according to claim 1 wherein the amount of A-QA1 complex immobilized at said test band is measured by contacting said mixture or said test band with a detection agent (DA1) capable of binding specifically to A in said A-QA1 complex.

3. A method according to claim 1 wherein said detection agent contains a detection moiety labeled directly or via labeled particles or microspheres.

4. A method according to claim 1, wherein the quantification agent is a binding partner of said analyte.

5. A method according to claim 1, wherein the binding partner immobilized in said test band is an antibody, antiserum, receptor, protein, peptide, oligonucleic acid, oligopeptide or nucleic acid.

6. A method according to claim 1, wherein the binding partner immobilized at said test band is a biotin-binding substance.

7. A method according to claim 2, wherein said detection agent is contacted with said mixture before said mixture is applied to the immunochromatographic device.

8. A method according to claim 2, wherein said detection agent is contacted with said mixture before said mixture enters into contact with said test band.

9. A method according to claim 2, wherein said detection agent is contacted with said test band after said mixture has contacted said test band.

10. A method according to claim 2, wherein the detection agent is a binding partner of said analyte.

11. A method of quantification of an analyte, A, in a test sample by means of a single lateral flow immunochromatographic device, consisting of the steps:
    a) mixing a determined amount of said test sample with a determined amount of a quantification agent, (QA1), said QA1 being capable of binding specifically and simultaneously both to an immobilized binding partner (BP) and to A, thus obtaining a mixture wherein the amount of A in said test sample is reflected by the ratio of the concentration of A-QA1 complex formed to the concentration of free QA1 in said mixture;
    b) applying a determined volume of said mixture to said device equipped with a test band in which said binding partner (BP) of the QA1 is immobilized, so that A-QA1 complex and free QA1 are immobilized at said test band in a ratio that relates to their concentration ratio in the mixture applied, said volume of mixture being determined to provide a total amount of A-QA1 complex and free QA1 that saturates binding at the immobilized binding partner (BP) in said test band;
    c) measuring the amount of said A-QA1 complex immobilized at the test band; and
    d) comparing the result obtained from the test sample with the results obtained from calibration samples containing known or allocated amounts of A and thus determining the amount of A in said test sample.

* * * * *